(12) United States Patent
Roessl et al.

(10) Patent No.: US 9,066,649 B2
(45) Date of Patent: Jun. 30, 2015

(54) APPARATUS FOR PHASE-CONTRAST IMAGING COMPRISING A DISPLACEABLE X-RAY DETECTOR ELEMENT AND METHOD

(75) Inventors: Ewald Roessl, Ellerau (DE); Klaus Juergen Engel, Aachen (DE); Gereon Vogtmeier, Aachen (DE); Dieter Geller, Aachen (DE); Gerhard Martens, Henstedt-Ulzburg (DE); Sebastian Siegmund Schusser, Aachen (DE); Thomas Koehler, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 341 days.

(21) Appl. No.: 13/514,383
(22) PCT Filed: Dec. 3, 2010
(86) PCT No.: PCT/IB2010/055571
§ 371 (c)(1), (2), (4) Date: Aug. 3, 2012
(87) PCT Pub. No.: WO2011/070493
PCT Pub. Date: Jun. 16, 2011

(65) Prior Publication Data
US 2012/0307966 A1    Dec. 6, 2012

(30) Foreign Application Priority Data
Dec. 10, 2009 (EP) .................................... 09178692

(51) Int. Cl.
*A61B 6/00* (2006.01)
*A61B 6/03* (2006.01)
(52) U.S. Cl.
CPC . *A61B 6/00* (2013.01); *A61B 6/032* (2013.01); *A61B 6/4021* (2013.01); *A61B 6/484* (2013.01); *A61B 6/4291* (2013.01); *A61B 6/4092* (2013.01)
(58) Field of Classification Search
CPC ............... A61B 6/484; A61B 6/4291; G01N 23/20075; G21K 2207/005; G21K 1/06
USPC ....................... 378/16, 19, 21, 36, 37, 62, 145
See application file for complete search history.

(56) References Cited

U.S. PATENT DOCUMENTS

| 5,812,629 A | 9/1998 | Clauser |
| 2007/0183562 A1 | 8/2007 | Popescu et al. |
| 2009/0238334 A1 | 9/2009 | Brahme et al. |

FOREIGN PATENT DOCUMENTS

| EP | 1731099 | 12/2006 |
| JP | 2006345290 | 12/2006 |

(Continued)

OTHER PUBLICATIONS

G.H. Chen et al., "Image Reconstruction for Fan-Beam Differential Phase Contrast Computer Tomography", Physics in Medicine and Biology, vol. 53, No. 4, Feb. 21, 2008, pp. 1015-1025.

(Continued)

*Primary Examiner* — Courtney Thomas

(57) ABSTRACT

An X-ray image acquisition apparatus employing phase-contrast imaging with enlarged field of view includes an X-ray source, an X-ray detector element having a detector size, a beam splitter grating and an analyzer grating. An object is arrangeable between the X-ray source and detector. The beam splitter grating and the analyzer grating are arrangeable between the X-ray source and detector. The X-ray source, the beam splitter grating, the analyzer grating and the X-ray detector are operatively coupled such that a phase-contrast image of the object is obtainable. The apparatus is configure to acquire a phase-contrast image having a field of view larger than the detector size. The X-ray detector element is displaceable where, by the displacement of the X-ray detector, a phase-contrast image of the enlarged field of view is obtainable.

20 Claims, 5 Drawing Sheets

(56) References Cited

FOREIGN PATENT DOCUMENTS

| | | |
|---|---|---|
| JP | 2007203061 | 8/2007 |
| JP | 2008545981 | 12/2008 |

OTHER PUBLICATIONS

W. Ge et al., "An Outlook on X-Ray CT Research and Development", Medical Physics, AIP, vol. 35, No. 3, Feb. 25, 2008, pp. 1051-1064.

F. Pfeiffer et al., High-Resolution Brain Tumor Visualization Using Three-Dimensional X-Ray Phase Contrast Tomography; High-Resolution Brain Tumor Visualization Using X-Ray Phase Contrast Tomography, Physics in Medicine and Biology, vol. 52, No. 23, Dec. 7, 2007, pp. 6923-6930.

T. Weitkamp et al., "X-Ray Phase Radiography and Tomography of Soft Tissue Using Grating Interferometry", European Journal of Radiology, vol. 68, No. 3, Dec. 1, 2008, pp. S13-S817.

Z. Wang, et al., "Differential Phase-Contrast Tomosynthetic Experimental System With Weakly Coherent Hard X-Rays", Nuclear Science Symposium Conference Record, 2008. NSS 2008, IEEE, Oct. 19-25, 2008, pp. 3889-3891.

Pfeiffer et al, "Hard X-Ray Phase Tomography With Low-Brilliance Source", Physical Review Letters, 98, 108105, 2007, pp. 1-4.

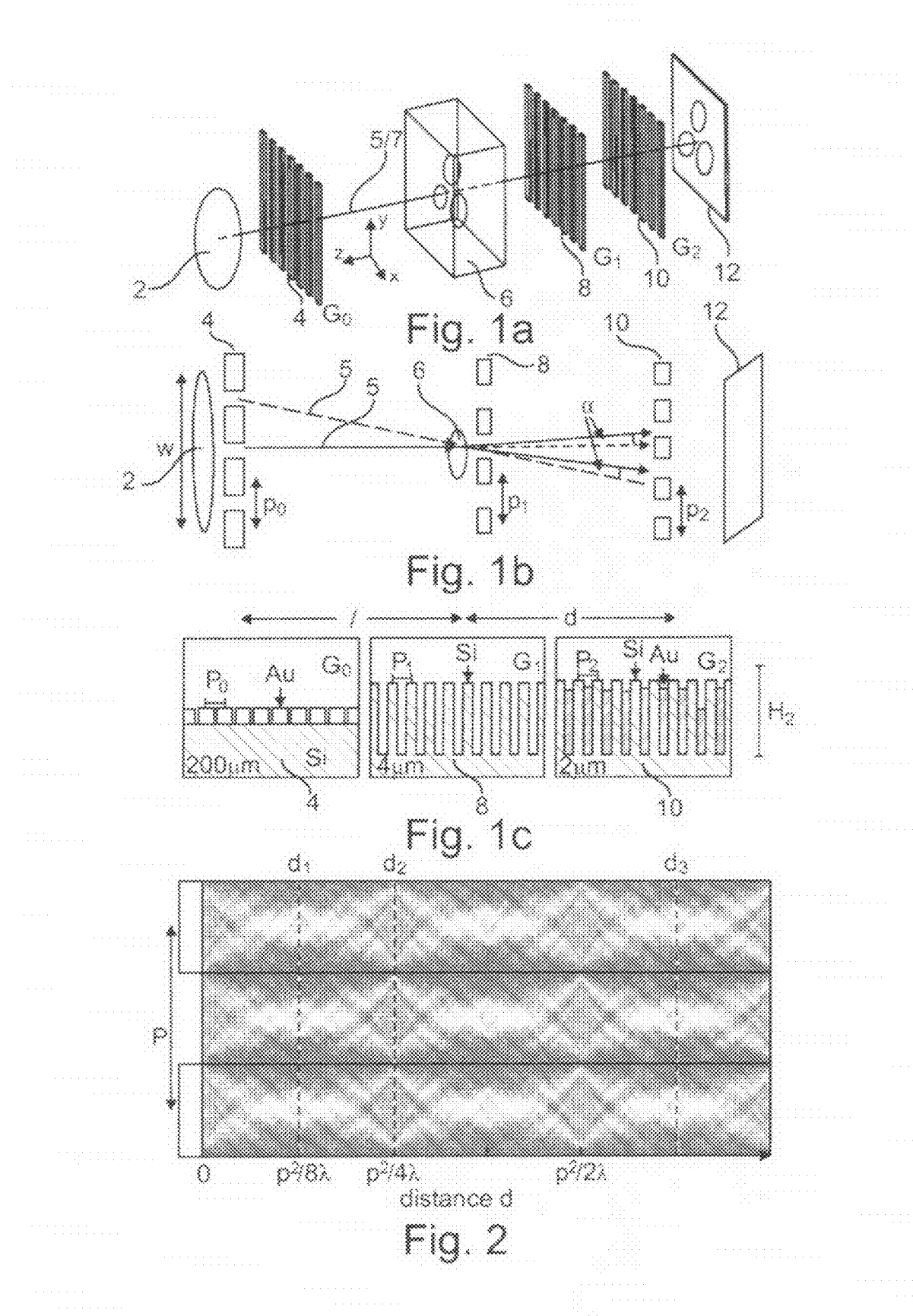

APPARATUS FOR PHASE-CONTRAST IMAGING COMPRISING A DISPLACEABLE X-RAY DETECTOR ELEMENT AND METHOD

FIELD OF THE INVENTION

The present invention relates to X-ray image acquisition in general. More particularly, the present invention relates to image acquisition employing phase-contrast. In particular, the present invention relates to an apparatus for phase-contrast imaging comprising a displaceable X-ray detector element, an X-ray system, a method for acquiring phase-contrast image information and the use of an apparatus for phase-contrast imaging in one of an X-ray system, a CT system and a tomosynthesis system.

BACKGROUND OF THE INVENTION

In X-ray image acquisition technology, an object to be examined, e.g. a patient, is situated between an X-ray generating device or X-ray source, e.g. an X-ray tube, and an X-ray detector. A fan-beam or cone-beam is generated by the X-ray source, possibly employing collimation elements, in the direction of the X-ray detector. The object to be examined situated in the path of the X-radiation is spatially attenuating the X-ray beam, depending on its inner structure. The spatially attenuated X-radiation is subsequently arriving at the X-ray detector, with the intensity distribution of the X-radiation being determined and subsequently converted to electrical signals for further processing and display of an X-ray image.

Both the X-ray generating device and the X-ray detector may be mounted on a gantry for rotation about the object to be examined. By providing an according rotation with subsequent acquisition of different X-ray images of varying alignment and orientation with respect to the object to be examined, a three-dimensional reconstruction of the objects inner morphology may be obtained.

However, a certain object may have only a minor attenuation of X-radiation or differences in attenuation even within different tissues in the inside of the object, thus resulting in a rather uniformly attenuated X-ray image having low contrast and so impeding distinguishing individual elements of the interior of the object to be examined. While different regions within the object may have similar attenuation properties, they may influence a phase of X-radiation penetrating the object to a larger extent.

Thus, phase-contrast imaging may be employed for visualization of phase information of X-radiation, in particular coherent X-rays, passing an object to be examined. In addition to X-ray transmission imaging taking into account only amplitude attenuation of X-radiation, phase-contrast imaging may not only determine absorption properties of an object to be examined along a projection line, but also the phase-shift of transmitted X-rays. A detected phase-shift may thus provide additional information that may be employed for contrast enhancement, determining a material composition, possibly resulting in a reduction in X-radiation dosage.

Since a phase of a wave may not be measured directly, a conversion of a phase-shift into an intensity modulation by interference of two or more waves may be employed.

In differential phase contrast imaging, the use of a cone-beam geometry may constitute a limitation of the usable size of an X-ray detector element, in particular when the phase and/or the absorption gratings are aligned with their trenches parallel to the optical axis. At a distance of about 1 m from the x-ray source, the point where the phase-sensitivity drops significantly with respect to the central region of the imaging system is about +−3 cm off the optical axis.

For some applications, e.g. medical imaging applications, inspection imaging applications or security imaging applications, a field of view of under 6 cm, at least in one direction of a two-dimensional X-ray image may be too small to be feasibly reasonable.

Thus, there may be a desire to increase the field of view when employing phase-contrast imaging.

SUMMARY OF THE INVENTION

Accordingly, an apparatus for phase-contrast imaging with an increased field of view, an X-ray system comprising an apparatus for phase-contrast imaging, a method for acquiring phase-contrast image information and the use of an apparatus for phase-contrast imaging in one of an X-ray system, a CT system and a tomosynthesis system according to the independent claims are provided.

According to an exemplary embodiment of the present invention, an apparatus for phase-contrast imaging is provided, comprising an X-ray source, an X-ray detector element having a detector size, a first grating element and a second grating element. An object is arrangeable between the X-ray source and the X-ray detector and the first grating element and the second grating element are also arrangeable between the X-ray source and the X-ray detector. The first grating element, the second grating element and the X-ray detector are operatively coupled such that a phase-contrast image of the object is obtainable. The phase-contrast image comprises phase-contrast image information, having a field of view larger than the detector size. The X-ray detector element is displaceable, wherein by the displacement of the X-ray detector a phase-contrast image of the field of view is obtainable.

According to a further exemplary embodiment of the present invention, an X-ray system is provided, comprising an apparatus for phase-contrast imaging according to the present invention.

According to a further exemplary embodiment of the present invention, a method for acquiring phase-contrast image information is provided, comprising the steps of acquiring first phase-contrast image information in a first phase stepping state, displacing, tilting and/or rotating an X-ray detector element relative to at least one of an object to be examined and an X-ray source and displacing a first grating element and a second grating element relative to one another. Second phase-contrast image information is acquired comprising a second phase stepping state.

According to a further exemplary embodiment of the present invention, an apparatus for phase-contrast imaging according to the present invention is used in at least one of an X-ray system, a CT system and a tomosynthesis system.

For obtaining phase information of an X-ray beam an interferometer may be employed. Preferably coherent X-radiation passes through an object to be examined subsequently arriving at an X-ray detector. Since phase information may not be measured directly, the implications of a constructive or destructive interaction of two or more wave fronts, possibly resulting in an intensity modulation detectable by an X-ray detector, may be employed.

An according interference may be obtained by providing a phase-shifting grating or a beam splitter grating between the object to be examined and the X-ray detector. X-radiation passing the beam splitter grating thus results in an interference pattern behind the beam splitter grating, containing information about a phase-shift within the X-ray beam in the relative positions of its minima and maxima, i.e. the respective local intensity of the X-ray beam. The resulting intensity pattern comprises minima and maxima having a distance typically in the order of several micrometers.

However, an X-ray detector may only comprise a resolution in the order of 50 to 150 μm and may thus not be able to resolve an accordingly fine structure of the generated interference pattern. Accordingly, a phase analyzer grating or absorber grating may be employed, comprising a periodic pattern of transmitting and absorbing strip elements or trench regions and blocking regions, having a periodicity similar to that of the interference pattern.

By illumination of the beam splitter grating alone, an interference pattern may be generated at the location of the analyzer grating, even in the absence of the latter. The analyzer grating may thus only be required due to x-ray detector elements employed, which do not provide a spatial resolution high enough to detect the interference pattern or fringes of the beam slitter grating directly. Because of this, the analyzer may be employed. In one phase-stepping position, it lets the fringe maxima pass through to the detector, after transverse displacement, the maxima may be absorbed in the gold trenches.

By the similar periodicity of the analyzer grating, a Moiré pattern may be generated behind the analyzer grating on the surface of the X-ray detector. An according Moiré pattern may have a substantially larger periodicity, which may thus be detectable by an X-ray detector having a resolution in the order of 50 to 150 μm. To obtain a phase-contrast image, in particular for obtaining the differential phase-shift, the analyzer grating may be required to be shifted laterally, i.e. in a direction perpendicular to the grids or strips of both the analyzer grating and the beam splitter grating, which gratings are arranged substantially parallel with regard to the grating strips, by fractions of the grating pitch p, which may be in the order of 1 μm. E.g., the position from one grating gap or trench region to a subsequent grating gap may be changed in the order of e.g. 4 times or 8 times. An according lateral shift by fractions of the grating pitch p may be referred to as phase stepping. An X-ray beam passing through the grating in a single phase stepping instance thus comprises an individual phase stepping state.

The phase-shift may then be extracted from the intensity modulation observed in the X-ray detector element behind both grids during the phase stepping measured for each position, e.g. for each phase stepping state, of the analyzer grating. Due to an incident angle of the X-rays onto the gratings, the visibility may be seen as decreasing for larger off axes positions with regard to a lateral extension to the trenches of the gratings. To assure sufficient visibility and thus detectability of the x-ray phase by the X-ray detector, a field of view may be limited to the size of about 6 cm, e.g. in case of system lengths, the distance between X-ray source and X-ray detector element, of about 1 m and energies of about 20-30 kVp. One solution to increase the field of view may be seen as moving an X-ray detector thus obtaining multiple sub-regions of a field of view subsequently. Since for each position of the X-ray detector a phase stepping, i.e. e.g. 4 or 8 individual image acquisitions having a different phase stepping state, may be required an according movement, displacement, tilt or rotation of an X-ray detector combined with an according phase stepping may be a prolonged process.

The possible requirement of the field of view being less than 6 cm at least in one direction or extension, use of planar detectors may be limited in phase-contrast imaging like e.g. differential phase-contrast mammography. A solution to overcome the limitation of the field of view may be employing multi-tile detectors, e.g. detectors comprising multiple detector elements, possibly angled towards one another with respect to the detector plane, and/or scanning the tiles or detector over the field of view, thus acquiring multiple subsequent images constituting a larger field of view.

In conventional absorption contrast projection imaging, a multitude of object structures along the direction of the incoming X-rays is superimposed in the image. This may often complicate determining individual structures and thus diminish the readability of an according X-ray image. An improvement in image quality may be obtained by distributing the total radiation dose over several angular views for improving depth information about the objects inner structure. An according technique may be referred to as tomosynthesis. An according system may require the X-ray source and the X-ray detector being arranged on a gantry for rotation about the object to be examined.

Even in phase-contrast imaging a single projection may comprise superimposed structures and thus may also benefit from a tomosynthesis mode of operation. Accordingly, employing a phase-contrast system capable of tomosynthesis may overcome the diminished readability by superposition of anatomical structures.

The requirement of sufficient fringe visibility of, e.g. sufficiently large intensity modulations in phase-contrast imaging, in particular differential phase-contrast imaging, may impose restriction on the degrees of freedom of relative motion between an X-ray source and the gratings. In general, only a relative movement of the X-ray source along the grating trenches may be permitted. Thus, by providing a tomosynthesis movement in the direction parallel to the trenches of the silicon grids of the gratings compatibility between tomosynthesis and phase-contrast imaging may be achieved. Thus, it may be seen as being beneficial for the angle of incidence, measured within a plane perpendicular to the grating trenches, of X-radiation onto the gratings to not increase above a certain level during a tomosynthesis scan.

Extending the field of view by moving the X-ray detector thus scanning the X-ray detector through the field of view may require performing phase stepping for each position of the X-ray detector within the field of view. E.g., in a particular position a phase stepping of 4 or 8 image acquisition steps each having a different phase stepping state may be required. Subsequently, the X-ray detector may be displaced to acquire a sub-region of the field of view substantially adjacent to the previous arrangement within the field of view subsequently employing phase stepping with 4 or 8 image acquisition steps for acquiring phase-contrast image information of the second sub-region of the field of view.

However, the X-ray detector may not be required to be displaced in the magnitude of the extension or width of the X-ray detector itself, but may rather be displaced only by a fraction, like ¼ or ⅛ of the extension of the X-ray detector or its active area for X-ray acquisition, with a concurrent phase stepping to acquire X-ray image information not only of a slightly different sub-region of the field of view, possibly overlapping with the previous sub-region by ¾ or ⅞ but also having a different phase stepping state required for the subsequent generation of X-ray image information employing phase-contrast.

An according displacement may be implemented by an additional translational element on either one of the X-ray detector, beam splitter grating or the analyzer grating or even possibly on a further source grating. A simple displacement of the X-ray detector, the beam splitter grating and the analyzer grating without altering the relationship of the individual elements relative to one another, may result in the incapability of acquiring image information for phase-contrast imaging.

From a practical point of view, e.g. with regard to manufacturing an apparatus according to the present invention, the trenches of the gratings may preferably be perpendicular to the flat surface of the X-ray detector.

Conventionally, the beam-splitter grating and the analyzer grating may be manufactured from silicon wafers. For the analyzer grating, a further electro-plating process may be required, in order to fill the trenches with a highly absorbing material, e.g. gold. The manufacturing process may e.g. start with the application of a passivation layer followed by an etching procedure. The regions covered by the passivation layer may not be affected by the etching process, thus resulting in a trench pattern typically required. However, it may be difficult to etch trenches in a direction different from the direction perpendicular to the wafer surface. For a cone-beam x-ray phase-contrast system, the etch direction may depend strongly on the position on the wafer, such that the trenches may be focused to a predefined position designed to coincide later with the x-ray source position.

An according arrangement may be seen as being in particular responsible for reducing visibility of structures when departing from the optical axis in the range of about 6 cm. In particular, a distance of about 1 m between X-ray source and X-ray detector may limit the detector size to about 6 cm, e.g. in case of about 20-30 keV.

For overcoming an according limitation of detector size, a tiled detector may be employed, possibly comprising individual detector elements being angled towards one another with regard to the X-ray source or the focal spot of an X-ray generating device. An according arrangement of detector elements may be seen as orienting the surface normal of the individual detector elements towards, thus in the direction of the X-ray source and its focal spot respectively, at least when considered in a two-dimensional cross-section perpendicular to the trenches of the gratings.

Accordingly, each detector element can be seen as having its own, individual optical axis being directed towards and aligned with the X-ray source. The limitation of the detector size being about 6 cm may be seen as applying to each individual detector element individually. However, employing an X-ray detector being composed of at least two or a plurality of detector element introduces gaps in the detection area between the tiles or detector elements. Within the gaps, image acquisition may not be performed. In certain areas of X-ray image acquisition, e.g. mammography applications, where structures of a few ten to 100 µm are to be detected, loss of image information due to undetectability within gaps between X-ray detector elements may not be acceptable.

Since phase-contrast imaging already requires each geometrical ray from the X-ray source to a detector pixel being measured multiple times e.g. 4, 8 or 9 times, with relative positions of the gratings, thus individual phase stepping states, phase stepping may be combined with a movement, e.g. displacement, tilting or rotation of the X-ray detector in combination with the phase stepping.

By employing an according movement, each geometrical array may thus only coincide once with a gap of a tiled detector array, thus providing a sufficient number of measurements for each geometrical ray for phase retrieval and for subsequent generation of a phase-contrast image. E.g., between different illuminations of the detector required for phase retrieval, the detector as a whole may be moved with the focal spot as rotation axis, in particular tilted towards the focal spot or X-ray source such that the surface normals of the individual detector elements may be focused towards the focal spot of the X-ray source.

By adapting the rotation or movement of the detector, it may be achievable that each geometrical ray coincides only once during the entire acquisition with gaps between the tiles thus phase retrieval may be possible for the entire detector area with the gaps between the detector elements not being visible after image acquisition. E.g., when employing a phase stepping requiring N=8 individual phase stepping states per geometrical ray by an according rotation or movement, all of the geometrical rays will be measured 8 times if the detector is moved for each step by $$\Delta x = \frac{D+G}{N+1}$$

where D is the detector width and G is the width of the gap. This requires altogether 9 image acquisitions. Additionally one needs to insure that the displacement $\Delta x$ is larger than the gap, a requirement that may be easily met, since usually D is large compared to the gap G: D>>G. For example one may realize a slight overlap by implementing:

$\Delta x \geq 2G$

The acquisition of medical images of diagnostic quality usually requires a gapless coverage of a certain field-of-view surrounding a given object of interest. This coverage may automatically be established by employing large-area pixelated detection units, thus X-ray detectors, so that for all neighbouring geometrical rays, falling within the solid angle covered by the detector or at least a detector pixel, imaging information is available. This may cede to be the case for several detector elements aligned next to each other, in particular possibly comprising a gap or separation distance. Henceforth, a geometrical ray may be considered to be a fixed line in the reference frame attached to the object of interest. Thus, a geometrical ray may be a fixed line of sight that coincided, in one instance or image acquisition step, with an X-ray detector element pixel, pixel row or pixel column. For obtaining suitable image information, e.g. for phase contrast imaging, the same geometrical ray, in particular with respect to the X-ray source and a certain inner structure of the object to be examined, may be required to be acquired. An according geometrical ray may in particular have a dimensional extension related to the size of an X-ray detector element pixel, taking further into account a distance between the X-ray source and its focal spot respectively.

Phase-contrast imaging may be implemented beneficially when employing a coherent X-ray source. However, since a coherent X-ray source may in particular only be provided by e.g. a synchrotron, a further grating, a source grating, may be employed between the X-ray source and the object in the beam path of the X-rays for generating a plurality of individual coherent X-ray sources.

Further, phase-contrast imaging may be performed by also employing two absorption gratings, instead of one phase and one absorption grating. A phase stepping in accordance with the present patent application may thus be required as well.

Also, it may be required to collimate X-radiation dynamically with regard to a moving X-ray detector element for assuring that only X-radiation detected is allowed to pass through the object.

Furthermore, each of the grating tiles may be focused along the propagation directions of the x-ray cone-beam. In the following, further embodiments of the present invention are described referring in particular the apparatus for phase-contrast imaging. However, these explanations also apply to the X-ray system, the method for acquiring phase-contrast image information and to the use of an apparatus for phase-contrast imaging in at least one of an X-ray system, a CT system and a tomosynthesis system.

The object may also be arranged between a first grating element and a second grating element, in particular between a beam splitter grating and an analyzer grating.

It should be noted that arbitrary variations and interchanges of single or multiple features between claims and in particular claimed entities are conceivable and within the scope and disclosure of the present patent application.

According to a further exemplary embodiment of the present invention, the displacement of the X-ray detector element may comprise rotating about at least one of the X-ray source and a focal spot of the X-ray source.

By a rotational movement of the X-ray detector element, the angle of the X-ray source and/or a focal spot of the X-ray source with regard to the trench structure of the grating elements, in particular the sidewalls of the trench structure, remains substantially identical during acquisition of phase contrast image information. Preferably, the angle is substantially zero with regard to the sidewalls of the grating elements, with a cone beam or fan beam of X-radiation impinging directly parallel to the sidewalls of the grating elements, at least with regard to the center of the grating elements.

According to a further exemplary embodiment of the present invention, the beam splitter grating and the analyzer grating are displaceable relative to one another for providing phase stepping and/or the beam splitter grating and the analyzer grating may be arranged parallel to one another and to the X-ray detector element.

Employing phase stepping for acquiring individual phase-contrast image information, e.g. intensity modulations during phase stepping, may allow reconstructing a representation of an inner structure of an object to be examined. The displacement of the splitter grating and the analyzer grating is preferably such that a plurality of displacements is arranged within one period of a grating. It is in particular beneficial to employ a displacement having e.g. ¼ or ⅛ of the period of a grating.

According to a further exemplary embodiment of the present invention, the X-ray source may be displaceable relative to the beam splitter grating, the analyzer grating and/or the X-ray detector element. Furthermore, the X-ray source, the beam splitter grating, the analyzer grating and the X-ray detector element may be rotatable about the object to be examined.

Such a displacement may be seen as positioning the X-ray source and the focal spot for generating X-radiation respectively in a different alignment with regard to the object to be examined and its inner morphology. Thus, by arranging the X-ray source differently with regard to the object, a tomosynthesis image acquisition may be provided.

According to a further exemplary embodiment of the present invention at least one of the first grating element and the second grating element may comprise a trench structure, wherein the trench structure may comprise a first extension parallel to the trench structure and the trenches respectively, and wherein the displacement of the X-ray source may be parallel to the first extension.

Thus, an angle between the X-ray source and the sidewalls of the grating elements may remain substantially unchanged during acquisition of phase contrast image information, at least with regard to a single phase contrast image.

According to a further exemplary embodiment of the present invention, the X-ray detector element may be displaceable from a first position for acquiring a first sub-region of the field of view to a second position for acquiring a second sub-region of the field of view and the beam splitter grating and the analyzer grating may be displaceable relative to one another for providing a first phase stepping state at the first position and a second phase stepping state at the second position.

In other words, when repositioning the detector element and the beam splitter grating as well as the analyzer grating, the beam splitter grating and the analyzer grating are further repositioned relative to one another, possibly by a fraction of the period of the grating of one of the beam splitter grating and the analyzer grating for obtaining a difference in phase stepping, thus different phase stepping states when acquiring a first image information at the first position and a second image information at the second position for allowing reconstruction phase-contrast image information.

According to a further exemplary embodiment of the present invention the apparatus further comprises at least two X-ray detector elements, at least two beam splitter gratings and at least two analyzer gratings. The at least two X-ray detector elements may be adjacently arranged and may be separated by a separation distance, possibly constituting a gap between the detector element pixels of the at least two detector elements, thus constituting a region or an area that may not be capable of acquiring image information. Each of the at least two X-ray detector elements may comprise a surface normal vector in the direction of the X-ray source and in the separation distance no image information may be acquired.

By employing at least two or a plurality of X-ray detector elements, possibly also employing a plurality of beam splitter gratings and analyzer gratings with an according angulation towards one another, the field of view of the X-ray detector comprising at least two detector elements may be enlarged, e.g. enlarged over 6 cm. The at least two beam splitter gratings and the at least two analyzer gratings may be individual elements or may also be adjacently arranged and thus connected to one another. It is also conceivable that one of a plurality of beam splitter gratings and analyzer gratings constitute a combined element, possibly having individual orientations in parallel to the at least two X-ray detector elements with the other plurality of the beam splitter gratings and the analyzer gratings being individual elements separated from one another and from the respective other grating for allowing a phase stepping.

In particular, the surface normal vector at a center of each of the X-ray detector elements may be considered to point towards the focal spot, at least in a 2 dimensional plane parallel to the grating trenches.

Most preferably, a detector element, a beam splitter grating and/or an analyzer grating may be provided having a cylindrical shape or a spherical shape with the X-ray source being arranged in the focus, thus equidistant to the surface of the X-ray detector element, the beam splitter grating and/or the analyzer grating.

According to a further exemplary embodiment of the present invention, the size of the at least two detector elements may substantially comprise the field of view of the image to be acquired.

Thus, by providing X-ray detector from at least two adjacently arranged detector elements each e.g. having a width of 6 cm or less, an image of a field of view larger than a single detector element may be acquired. Thus, an image having a field of view larger than what would normally be allowable with the respect of the dimensions of the individual detector elements may be acquired.

According to a further exemplary embodiment of the present invention the X-ray source may be displaceable about the object to be examined while the orientation of the surface normal vector of the at least two X-ray detector elements in the direction of the X-ray source may be maintained during the displacement of the X-ray source.

Maintaining the alignment of the X-ray detector elements in the direction of the X-ray source when displacing the X-ray source may allow acquiring a tomosynthesis phase-contrast image having a field of view larger than a single detector element, e.g. larger than 6 cm, for example 12, 18, 20, 24 or 30 cm. The orientation of the surface normal vector in the direction of the X-ray source may at least be maintained in a two-dimensional plane perpendicular to the grating trenches, thus a plane parallel to the surface normal vector.

According to a further exemplary embodiment of the present invention, the at least two X-ray detector elements may be displaceable from a first position and/or orientation for acquiring a first phase-contrast image to a second position and/or orientation for acquiring a second phase-contrast image and wherein each of the at least two first grating elements and each of the respective other of the at least two second grating elements may be displaced relative to one another for providing a first phase stepping state when acquiring the first phase-contrast image and a second phase stepping state when acquiring the second phase-contrast image.

Again, by providing a displacement being a fraction of the period of one of the two gratings, a different phase stepping state may be provided when acquiring a first phase-contrast image and a second phase-contrast image.

Each of the first grating elements is associated with a respective second grating element for acquiring phase contrast image information.

According to a further exemplary embodiment of the present invention, the at least two detector elements may be displaced, tilted and/or rotated between acquisition of two different phase-contrast images such that loss of image information that may not be acquired in the separation distance is minimized, in particular wherein the at least two X-ray detector elements may be displaced, tilted and/or rotated during acquisition of a phase contrast image such that each geometrical ray falls maximally into the unavoidable gaps between detector elements.

Accordingly, the two detector elements may be moved such that each geometrical ray in a successive number of phase-contrast image acquisitions, employing individual phase stepping states, coincides only once of the e.g. 4 or 8 individual image acquisition steps with the gap between the at least two detector elements and the separate distance respectively. In other words, if 8 measurements having a different phase stepping state for each geometric ray are required, 9 different measurements may be required to be performed. Thus, when taking n different measurements employing different phase stepping states for a respective geometrical ray, for each geometrical ray at least n−1 different measurement values may be obtained for subsequently determining a phase contrast image.

According to a further exemplary embodiment of the present invention, the apparatus may further comprise a source grating.

By providing a source grating between the X-ray source and the object in the path of the X-ray beam, a possibly incoherent X-ray source or an at least partially incoherent X-ray source may be employed for phase-contrast imaging.

According to a further exemplary embodiment of the present invention steps b; and c; may be repeated a defined number of times, in particular are repeated 8 times, constituting an acquisition cycle, wherein each geometrical ray may coincide maximally only once during the acquisition cycle with gaps between the tiles.

By employing an according acquisition cycle, a substantially uniform signal-to-noise ratio of the full acquired image may be achievable.

These and other aspects of the present invention will become apparent from and elucidated with reference to the embodiments described hereinafter.

Exemplary embodiments of the present invention will be described below with reference to the following drawings.

The illustration in the drawings is schematic. In different drawings, similar or identical elements are provided with similar or identical reference numerals.

Figures are not drawn to scale, however may depict qualitative proportions.

BRIEF DESCRIPTION OF THE DRAWINGS

FIGS. 1a-c show an exemplary embodiment of an apparatus for phase-contrast imaging according to the present invention, FIG. 2 shows an exemplary embodiment of an interference pattern according to the present invention, FIGS. 3a,b show exemplary phase-contrast images acquired according to the present invention.

DETAILED DESCRIPTION OF EMBODIMENTS

Figure 3A:
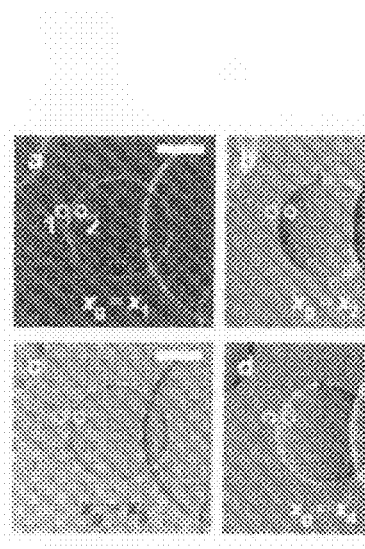
Figure 3B:
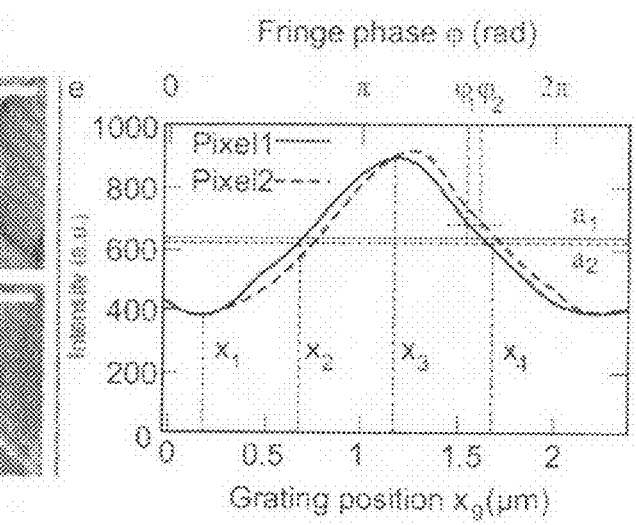

Now referring to FIGS. 1a-c, an exemplary embodiment of an apparatus for phase-contrast imaging according to the present invention is depicted.

FIG. 1a shows a three-dimensional representation of an exemplary embodiment of an apparatus for phase-contrast imaging. A rather large X-ray source 2 is arranged adjacent to a source grating 4. Since X-ray source 2 may be considered to be incoherent due to its size with respect to the wavelength of the radiation emitted, the source grating $G_0$ 4 is employed for providing a plurality of single coherent X-ray sources as depicted by the two arrows in FIG. 1b.

X-radiation 5 is emanating from X-ray source 2 in the direction of the optical axis 7 possibly constituting a fan-beam or cone-beam of X-rays. The respective shape of the X-ray beam is not depicted in FIG. 1a.

X-radiation 5 is arriving at object 6, penetrating object 6, subsequently arriving at a beam splitter grating $G_1$ 8. The trenches or gaps of the beam splitter grating 8 alter the phase of passing electromagnetic radiation with respect to the solid areas of the beam splitter grating, the blocking region. Accordingly, a phase shift by $\phi$, in particular by $\pi$, is performed.

An analyzer grating 10 $G_2$ is arranged between the beam splitter grating $G_1$ 8 and the X-ray detector 12. The distance between the source grating and the beam splitter grating 8 is depicted as l whereas the distance between the beam splitter grating 8 and the analyzer grating 10 is depicted as distance d. The multiple waves originating from the beam splitter grating 8 $G_1$ in the direction of the X-ray detector are arriving at the analyzer grating 10 $G_2$, subsequently producing an intensity modulation pattern (see FIG. 2) on the surface of the X-ray detector 12.

By shifting the beam splitter grating 8 versus the analyzer grating 10, thus displacing of gratings relative to one another, in particular with a fraction of the grating period $p_1$ or $p_2$, a plurality of intensity modulations induced by the phase stepping may be obtainable by the image detector 12, since the individual phase stepping states are different between individual phase steppings, i.e. alignment of $G_1$ versus $G_2$. Accordingly, by a plurality of Moiré patterns, an X-ray image of the object to be examined may be generated. Distance l may be of the order of 50-150 cm and distance d may be of the order of 2-20 cm, depending on the Talbot order chosen in the design of the interferometer.

Now referring to FIG. 1c, exemplary cross-sections of gratings $G_0$ to $G_2$ are depicted. Gratings $G_0$ and $G_2$ may in particular be filled with gold (Au). Gratings $G_1$ and $G_2$ may be implemented by etching a silicon based material for providing the trenches of the gratings. The grating period $p_0$ of the source grating may be in the order of 200 μm, even smaller, the grating period $p_1$ of $G_1$ may exemplary be 4 μm and the grating period $p_2$ of $G_2$ may exemplary be 2 μm.

Now referring to FIG. 2, an exemplary embodiment of an interference pattern according to the present invention is depicted.

FIG. 2 depicts an interference pattern created between beam splitter grating $G_1$ 8 and analyzer grating $G_2$ 10, demonstrating the self imaging effect of the grid in characteristic distances $d_1$, $d_2$ and $d_3$ (Talbot effect). The relative position of the minima and maxima may in particular depend on the phase-shift of the wave front incident on beam splitter grating $G_1$. $d_1$ may in particular be in the order of several cm. If a monochromatic plane wave is incident on the beam-splitter grating that induces a phase shift of $\phi$, in particular by $\pi$, the intensity is split into two main diffraction orders, cancelling the zeroth order. The interference effects lead to an effect of self-imaging of the wave-front incident on $G_1$ at discrete distances downstream from $G_1$. This effect is referred to as the Talbot effect. E.g. at a distance $p1^2/8$ lambda, the phase modulation of the incident wave-front induced by $G_1$ is transformed into an intensity modulation with double frequency. The analyzer grating samples these modulations and allows to measure the phase-gradient induced by an object onto the x-ray wave-front via phase-stepping.

Now referring to FIGS. 3a,b, exemplary phase-contrast images acquired according to the present invention is depicted.

In FIG. 3a, exemplary four images are acquired of an object comprising individual bubbles by phase stepping employing four phase steps and thus four individual phase stepping states a-d. Distances $x_1$-$x_4$ relate to a displacement of grids $G_1$ versus $G_2$ for creating an intensity modulation. The full movement from $x_1$-$x_4$ is within one period of grating $G_2$ (<2 μm). The absorber grid or analyzer grid $G_2$ 10 is shifted in a direction x parallel to the grating planes. The difference in the wave front phase at two positions "1" and "2" may be extracted from the phase-shift $\phi_1$-$\phi_2$ of the measured intensity modulation, e.g. for four sampling positions $x_1$-$x_4$ in FIG. 3a.

Figure 4:
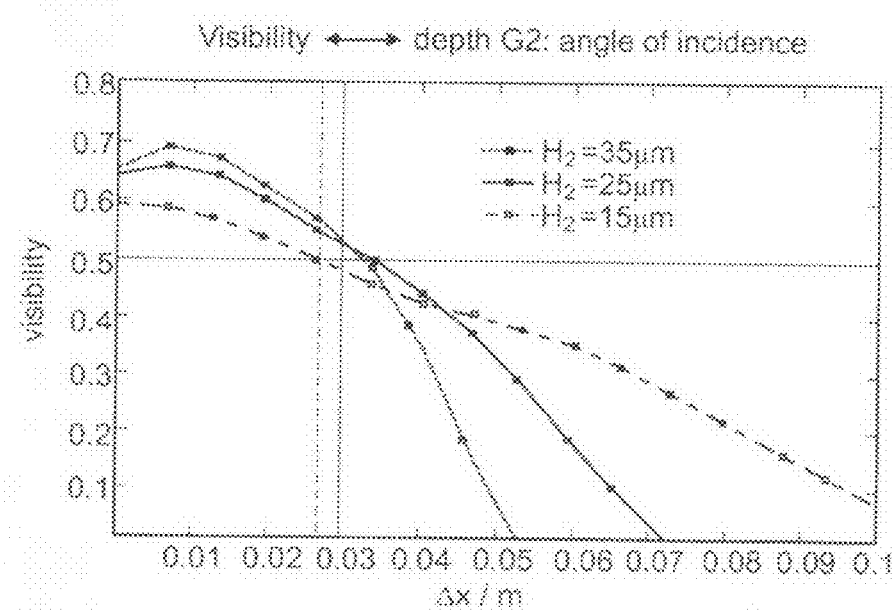
FIG. 4 shows exemplary visibility of interference fringes versus off axis position of a detector element pixel according to the present invention, FIGS. 5a,b show exemplary embodiments of tomosynthesis according to the present invention, FIGS. 6a,b show a three-dimensional and a two-dimensional representation of an exemplary embodiment of an X-ray detector comprising a plurality of detector elements according to the present invention.

Now referring to FIG. 4, exemplary visibility of interference fringes versus off axis position of a detector element pixel according to the present invention is depicted.

The degradation of the fringe visibility as a function of the off axis position of detector pixels may be taken from FIG. 4. A fringe visibility of 0.5 or greater may be considered to provide reasonable phase-contrast for image generation and processing. Three functions are provided in FIG. 4, depending on the height $H_2$ of the grating structure of grating $G_2$ (see FIG. 1c) providing deeper trenches in the grating, e.g. 35 μm, results in a diminished off axis visibility over a shallower grating depth $H_2$ of e.g. 15 μm. As may be taken from FIG. 4, a two-sided collimation has to be below 6 cm, thus Δx should be <3 cm, thereby limiting the usable size of planar detectors in phase-contrast imaging like e.g. differential phase-contrast mammography, to about 6 cm.

Figure 5A:
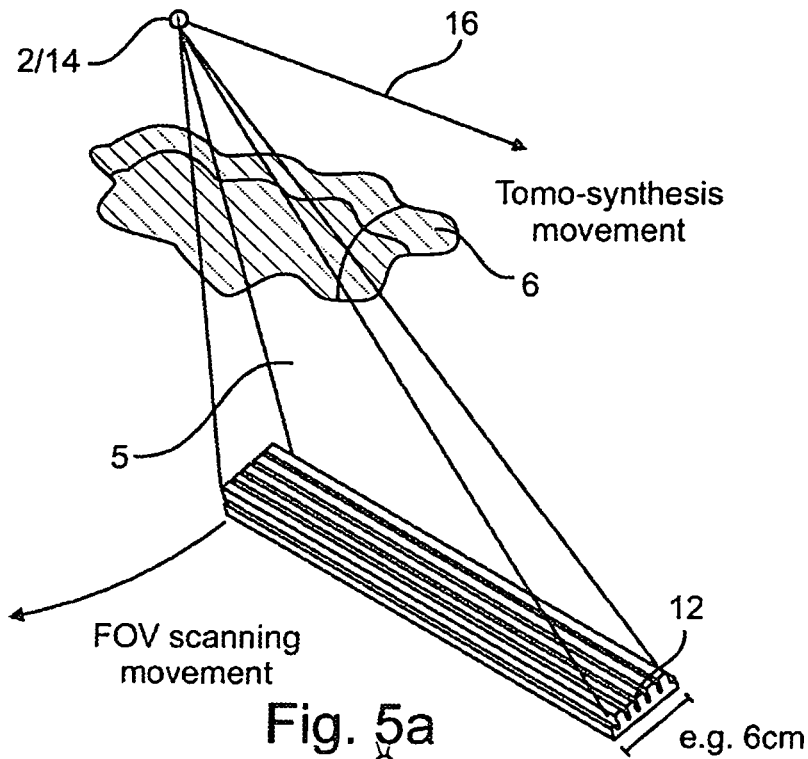

Now referring to FIGS. 5a,b, exemplary embodiments of tomosynthesis according to the present invention are depicted.

FIGS. 5a,b depict two possible realizations of phase-contrast tomosynthesis. In FIG. 5a the X-ray source 2 or focal spot 14 is displaced in a linear movement 16 about object 6 employing a cone-beam of X-radiation 5 for acquiring different X-ray views through object 6.

Movement 16 is substantially parallel to the trenches of the gratings employed for phase-contrast imaging, which are not depicted in FIGS. 5a,b.

Since the X-ray detector 12 has as an extension perpendicular to the trenches of the gratings of e.g. 6 cm, a scanning movement of the X-ray detector through the field of view FOV is required for obtaining an X-ray image of the object 6 which is sufficiently large. E.g. in mammography applications, a field of view of typically 20×30 or 30×40 cm may be required.

In FIG. 5a, the X-ray source 2 or the focal spot 14 may be considered to be moved independently of the X-ray detector 12, which is only performing the field of view scanning movement as depicted by the arrow in FIG. 5a.

Figure 5B:
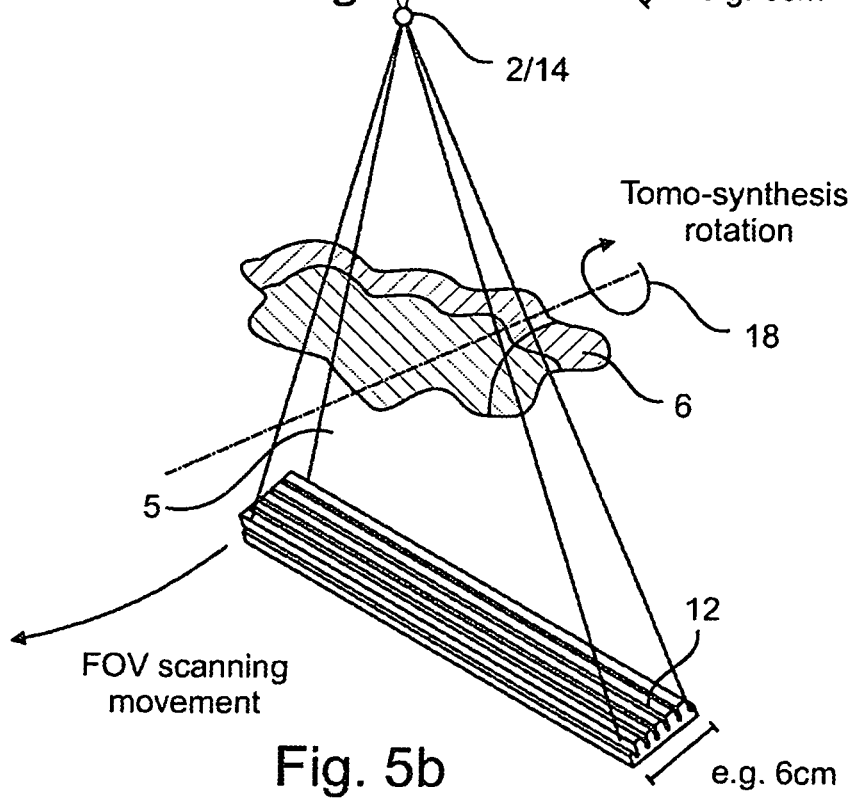

A further implementation may be seen in FIG. 5b. Both the X-ray source 2/focal spot 14 and the X-ray detector 12 may e.g. be mounted on a gantry for rotation about an axis 18, subsequently rotating both the X-ray source 2 and the X-ray detector 12 about object 6. An according movement may be compared to a regular movement in a computed tomography system.

In FIG. 5b, X-ray tube and X-ray detector are thus rotated simultaneously about object 6. Again, a further field of view scanning movement of the X-ray detector 12 in each individual position of the X-ray detector with regard to the field of view scanning movement, a phase stepping, is to be implemented for acquiring phase-contrast information. Accordingly, the X-ray detector 12 may be displaced substantially about its extension, thus e.g. 6 cm, subsequently providing phase stepping image information acquisition exemplary employing 4, 8 or 9 phase steps or may only be displaced by a fraction of the aforementioned 6 cm, e.g. ¼, ⅛ or ⅑ of its extension of 6 cm, with an accompanying, simultaneous phase stepping for providing an individual phase stepping state.

In order to implement phase stepping in a continuous fashion, e.g. grating $G_1$ may perform the field of view scanning movement slightly faster than the remaining elements of a sliding arm, e.g. by an additional translational element on the detector/$G_1$/$G_2$ arrangement. In other words, for each displacement of the X-ray detector 12, e.g. grating $G_1$ is displaced by the same distance or angle, depending on a linear or rotational movement, plus an additional A value for providing a further, new phase stepping state.

Figure 6A:
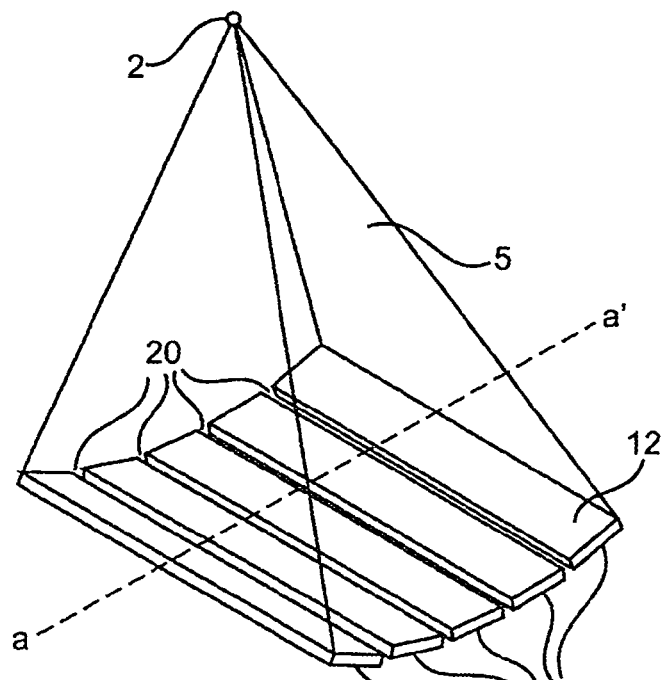

Now referring to FIGS. 6a,b, a three-dimensional and a two-dimensional representation of an exemplary embodiment of an X-ray detector comprising a plurality of detector elements according to the present invention is depicted.

In FIG. 6a, a tiled X-ray detector comprising exemplary five detector elements 12a-e is depicted. X-ray source 2 is emanating a cone-beam of X-rays 5, which, in the case of FIG. 6a, may be considered to constitute substantially the desired field of view.

Gaps 20 are arranged between the individual detector elements 12a-e, possibly being in the order of magnitude of 1 mm to 100 μm. A typical resolution, thus X-ray detector element pixel size, may be seen as 50 to 250 μm.

Collimation elements, not depicted in FIG. 6a, may dynamically collimate fan-beam 5 to substantially correspond to the area or current position of the of X-ray detector 12.

Figure 6B:
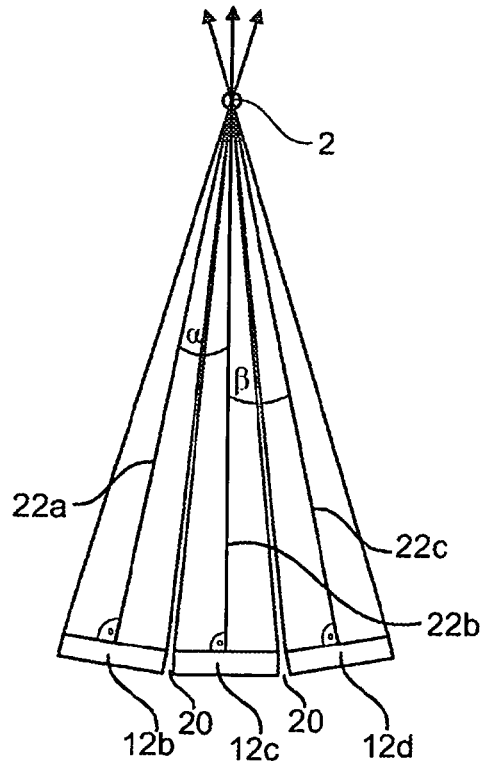
Figures 7A, 7B, 7C, 7D:
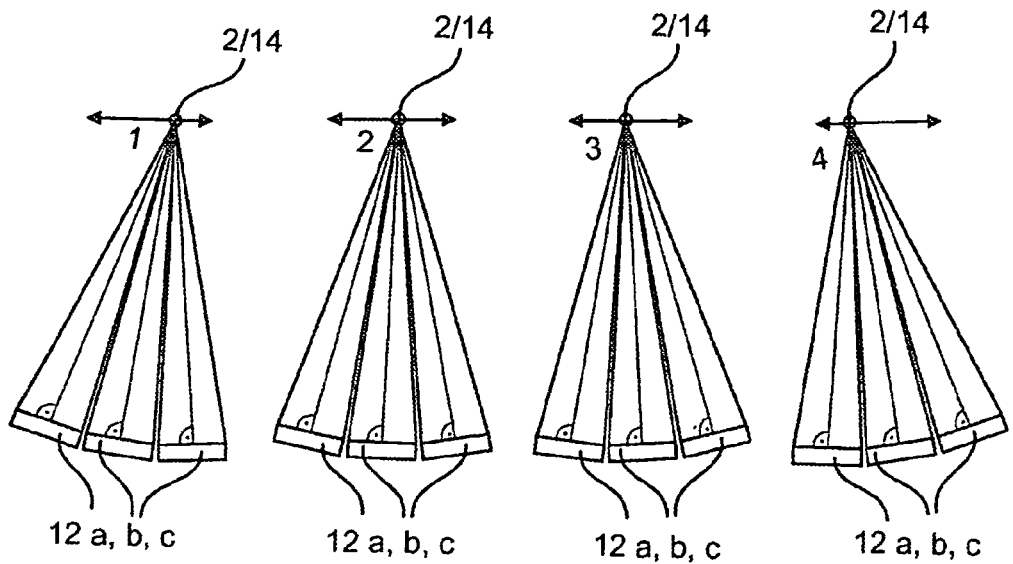
FIGS. 7a-d show an exemplary displacement of the focal spot with regard to a tiled X-ray detector according to the present invention.

Now referring to FIG. 6b, a two-dimensional image, cross-section along lines A-A' is depicted only showing detector elements 12b-d. Gaps 20 are arranged between detector 12b and c as well as between detector element 12c and d. A surface normal vector 22a,b,c is arranged on each surface of the individual X-ray detector element 12b,c,d in the direction of focal spot 2, possibly crossing focal spot 2. The individual detector elements 12b,c,d are angled towards one another by angles α and β, which in particular may be identical. Gratings $G_1$, $G_2$ and possibly $G_0$ are not depicted in FIGS. 6a,b. As may be seen in FIGS. 6a,b, gaps 20 between detector elements 12a-e are arranged such that no image information may be acquired within the gaps.

Now referring to FIGS. 7a-d, an exemplary displacement of the focal spot with regard to a tiled X-ray detector according to the present invention is depicted.

In FIGS. 7a-7d focal spot 14/X-ray source 2 is moved linearly for a tomosynthesis acquisition in accordance with FIG. 5a. A further rotation in accordance with FIG. 5b may be feasible as well.

The X-ray detector 12 comprising individual detector elements 12a,b,c is tilted so that surface normal vectors (22a,b,c,) of the individual X-ray detector elements 12a,b,c, are focused towards X-ray source 2, while X-ray source 2 is performing a translatory or linear movement. Between different illuminations of the X-ray detector 12 required for phase retrieval, the detector is moved, displaced and/or tilted with respect to the focal spot 14, in particular with the focal spot 14 as rotation axis or tilting axis. By an according rotation or tilt, it may be achievable that each geometrical ray coincides only once during the entire acquisition with gaps between the tiles. Accordingly phase retrieval is possible for the entire detector area here comprising detectors 12a,b,c with the gaps subsequently not being visible after phase retrieval in the image so obtained.

Grids $G_1$, $G_2$ and possibly $G_0$ are not depicted in FIGS. 7a-d, however are required for an additional phase stepping between individual image acquisitions 7a,b,c,d as explained earlier. A rotatory tomosynthesis movement in accordance with FIG. 5b is feasible as well.

Figure 8:
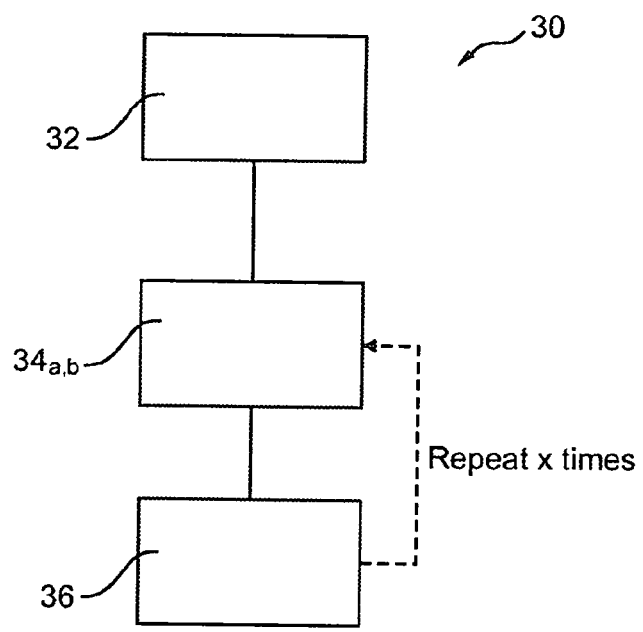
FIG. 8 shows an exemplary embodiment of a method for acquiring phase-contrast image information according to the present invention.

Now referring to FIG. 8, an exemplary embodiment of a method for acquiring phase-contrast image information according to the present invention is depicted.

In FIG. 8, a method 30 for acquiring phase-contrast image information is depicted comprising the steps of acquiring 32 first phase-contrast information in a first phase stepping state, displacing, tilting and/or rotating 34 an X-ray detector element relative to at least one of an object and an X-ray source and displacing a beam splitter grating and an analyzer grating relative to one another and acquiring 36 second phase-contrast image information in a second phase stepping state. Steps 34a,b and 36 may be repeated x times, e.g. 8 times, for a total of e.g. 9 acquisition steps with different, individual phase stepping states, for arriving at a full acquisition cycle, in which each geometrical ray coincides maximally only once during the entire acquisition with gaps between the tiles.

The displacement of the X-ray detector element and the displacement of the beam splitter grating versus the analyzer grating may be performed subsequently or concurrently.

It should be noted that the term "comprising" does not exclude other elements or steps and that "a" or "an" does not exclude a plurality. Also, elements described in association with different embodiments may be combined.

It should also be noted, that reference numerals in the claims shall not be construed as limiting the scope of the claims.

LIST OF REFERENCE NUMERALS

1 Apparatus for phase contrast imaging
2 X-ray source
4 Source grating $G_0$
5 X-radiation
6 Object
7 Optical axis
8 Beam splitter grating/phase grating $G_1$
10 Analyzer grating/absorber grating $G_2$
12(a-e) X-ray detector (element)
14 Focal spot
16 Linear movement
18 Rotation
20 Gap
22a,b,c Surface normal vector
30 Method for acquiring phase-contrast image information
32 STEP: Acquiring first phase-contrast image information
34a STEP: Displacing, tilting and/or rotating an X-ray detector element
34b STEP: Displacing a beam splitter grating and an analyzer grating relative to one another
36 STEP: Acquiring second phase-contrast image information

The invention claimed is:
1. An apparatus for phase contrast imaging, comprising:
an X-ray source;
an X-ray detector element having a detector size;
a first grating element; and
a second grating element;
wherein an object is arrangeable between the X-ray source and the X-ray detector element;
wherein the first grating element and the second grating element are arrangeable between the X-ray source and the X-ray detector element;
wherein the X-ray source, the first grating element, the second grating element and the X-ray detector element are operatively coupled such that a phase contrast image of the object is obtainable;
wherein the apparatus is configured to acquire a phase contrast image having a field of view larger than the detector size;
wherein the X-ray detector element is displaceable; and
wherein by the displacement of the X-ray detector element a phase contrast image of the field of view is obtainable.

2. The apparatus according to claim 1,
wherein the displacement of the X-ray detector element comprises rotating about at least one of the X-ray source and a focal spot of the X-ray source.

3. The apparatus according to claim 1,
wherein the first grating element and the second grating element are one of a beam splitter grating and an analyzer grating;
wherein the first grating element and the second grating element are displaceable relative to one another for providing phase stepping; and/or
wherein the first grating element and the second grating element are arranged parallel to one another and to the X-ray detector element.

4. The apparatus according to claim 1,
wherein the x-ray source is displaceable relative to the first grating element, the second grating element and/or the X-ray detector element.

5. The apparatus according to claim 1,
wherein the x-ray source, the first grating element, the second grating element and the X-ray detector element are rotatable about the object.

6. The apparatus according to claim 4,
wherein at least one of the first grating element and the second grating element comprises a trench structure including trenches;
wherein the trench structure comprises a first extension parallel to the trench structure and the trenches respectively; and
wherein the displacement of the X-ray source is parallel to the first extension.

7. The apparatus according to claim 1, wherein the X-ray detector element is configured to acquire a sub-region of the field of view; and
wherein, when the X-ray detector element is displaceable from a first position for acquiring a first sub-region of the field of view to a second position for acquiring a second sub-region of the field of view, the first grating element and the second grating element are displaced relative to one another for providing a first phase stepping state at the first position and a second phase stepping state at the second position.

8. The apparatus according to claim 1,
further comprising
at least two X-ray detector elements;
at least two first grating elements; and
at least two second grating elements;
wherein the at least two X-ray detector elements are adjacently arranged;
wherein the at least two X-ray detector elements are separated by a separation distance;
wherein each of the at least two X-ray detector elements comprises a surface normal vector in a direction of the X-ray source; and
wherein in the separation distance no image information may be acquired.

9. The apparatus according to claim 8, wherein the x-ray source is displaceable about the object; and
wherein orientation of the surface normal vector of the at least two X-ray detector elements in the direction of the X-ray source is maintained during the displacement of the X-ray source.

10. The apparatus according to claim 8,
wherein the at least two X-ray detector elements are displaceable from a first position and/or orientation for acquiring a first phase contrast image to a second position and/or orientation for acquiring a second phase contrast image, and
wherein each of the at least two first grating elements and each of the respective other of the at least two second grating elements are displaced relative to one another for providing a first phase stepping state when acquiring the first phase contrast image and a second phase stepping state when acquiring the second phase contrast image.

11. The apparatus according to claim 8,
wherein the at least two X-ray detector elements are displaced, tilted and/or rotated between acquisition of two different phase contrast images such that image information that may not be acquired in the separation distance is minimized.

12. Use of an apparatus for phase contrast imaging according to claim 1 in one of an X-ray system, a CT system and a tomosynthesis system.

13. The apparatus according to claim 8, wherein the at least two X-ray detector elements are displaced, tilted and/or rotated during acquisition of the phase contrast image such that each geometrical ray coincides maximally once with the separation distance.

14. The apparatus according to claim 1, wherein the X-ray detector element is displaceable by a predetermined value from a first position for acquiring a first sub-region of the field of view to a second position for acquiring a second sub-region of the field of view, and wherein at least one of the first grating element and the second grating element is displaced relative to one another by an additional value in addition to the predetermined value.

15. The apparatus according to claim 7, wherein the at least two X-ray detector elements are displaceable from the first position by a predetermined value, and wherein at least one of the at least two first grating elements and the at least two second grating elements are displaced relative to one another by an additional value in addition to the predetermined value.

16. An X-ray system, comprising an apparatus for phase contrast imaging, the apparatus comprising:
an X-ray source;
an X-ray detector element having a detector size;
a first grating element; and
a second grating element;
wherein an object is arrangeable between the X-ray source and the X-ray detector element;
wherein the first grating element and the second grating element are arrangeable between the X-ray source and the X-ray detector element;
wherein the X-ray source, the first grating element, the second grating element and the X-ray detector element are operatively coupled such that a phase contrast image of the object is obtainable;
wherein the apparatus is configured to acquire a phase contrast image having a field of view lamer than the detector size;
wherein the X-ray detector element is displaceable; and
wherein by the displacement of the X-ray detector element a phase contrast image of the field of view is obtainable.

17. A method for acquiring phase contrast image information, comprising acts of:
acquiring first phase contrast image information in a first phase stepping state;
displacing, tilting and/or rotating an X-ray detector element relative to at least one of an object and an X-ray source and displacing a first grating element and a second grating element relative to one another; and acquiring second phase contrast image information in a second phase stepping state.

18. The method according to claim 17,
wherein the displacing and acquiring acts are repeated a defined number of times constituting an acquisition cycle; and
wherein each geometrical ray coincides maximally only once during the acquisition cycle with gaps between a plurality of X-ray detector elements.

19. The method according to claim 17, wherein the displacing and acquiring acts are repeated 8 times constituting an acquisition cycle; and
wherein each geometrical ray coincides maximally only once during the acquisition cycle with gaps between a plurality of X-ray detector elements.

20. The method according to claim 17, wherein the displacing, tilting and/or rotating act displaces, tilts and/or rotates the X-ray detector element relative to the at least one of the object and the X-ray source by a predetermined value, and wherein the act of displacing the first grating element and the second grating element relative to one another displaces at least one of the first grating element and the second grating element relative to one another by an additional value in addition to the predetermined value.

* * * * *